United States Patent [19]

Lemelson et al.

[11] Patent Number: 5,728,123
[45] Date of Patent: Mar. 17, 1998

[54] BALLOON ACTUATED CATHETER

[76] Inventors: Jerome H. Lemelson, Suite 286, Unit 802 930 Tahoe Blvd., Incline Village, Nev. 89451-9436; J. Kevin Parker, 551 Green Bay Rd., Highland Park, Ill. 60035

[21] Appl. No.: 429,063

[22] Filed: Apr. 26, 1995

[51] Int. Cl.⁶ .................................................. A61B 17/20
[52] U.S. Cl. .................... 604/22; 604/43; 604/101; 604/102; 606/159; 606/180
[58] Field of Search ........................... 604/22, 101, 102, 604/43, 53; 606/159, 170, 191, 192, 194, 180

[56] References Cited

U.S. PATENT DOCUMENTS

| | | | |
|---|---|---|---|
| 4,636,195 | 1/1987 | Wolinsky . | |
| 4,990,139 | 2/1991 | Jang | 604/101 |
| 5,176,693 | 1/1993 | Pannek, Jr. | 606/159 |
| 5,181,920 | 1/1993 | Mueller et al. | 606/159 |
| 5,196,024 | 3/1993 | Barath | 606/159 |
| 5,222,966 | 6/1993 | Perkins et al. | 606/194 X |
| 5,320,599 | 6/1994 | Griep et al. | 606/159 X |
| 5,336,234 | 8/1994 | Vigil et al. | 606/171 X |
| 5,370,651 | 12/1994 | Summers | 606/159 |
| 5,417,703 | 5/1995 | Brown et al. | 606/159 |
| 5,462,529 | 10/1995 | Simpson et al. . | |

*Primary Examiner*—Mark Bockelman

[57] ABSTRACT

A catheter device for performing atherectomy procedures and the like in which cutting blades at the distal end of the catheter are extended by the application of fluid pressure to the catheter to inflate a balloon. One or more cutting blades are attached to the end of a resilient support that maintains the blade in a retracted position until engaged by the expanding balloon to extend the blade radially outward. Specific embodiments include separate expandable balloons provided on each side of the cutting blade to isolate the operative site and separate conduits for the infusion of a flushing liquid to the operative site.

13 Claims, 3 Drawing Sheets

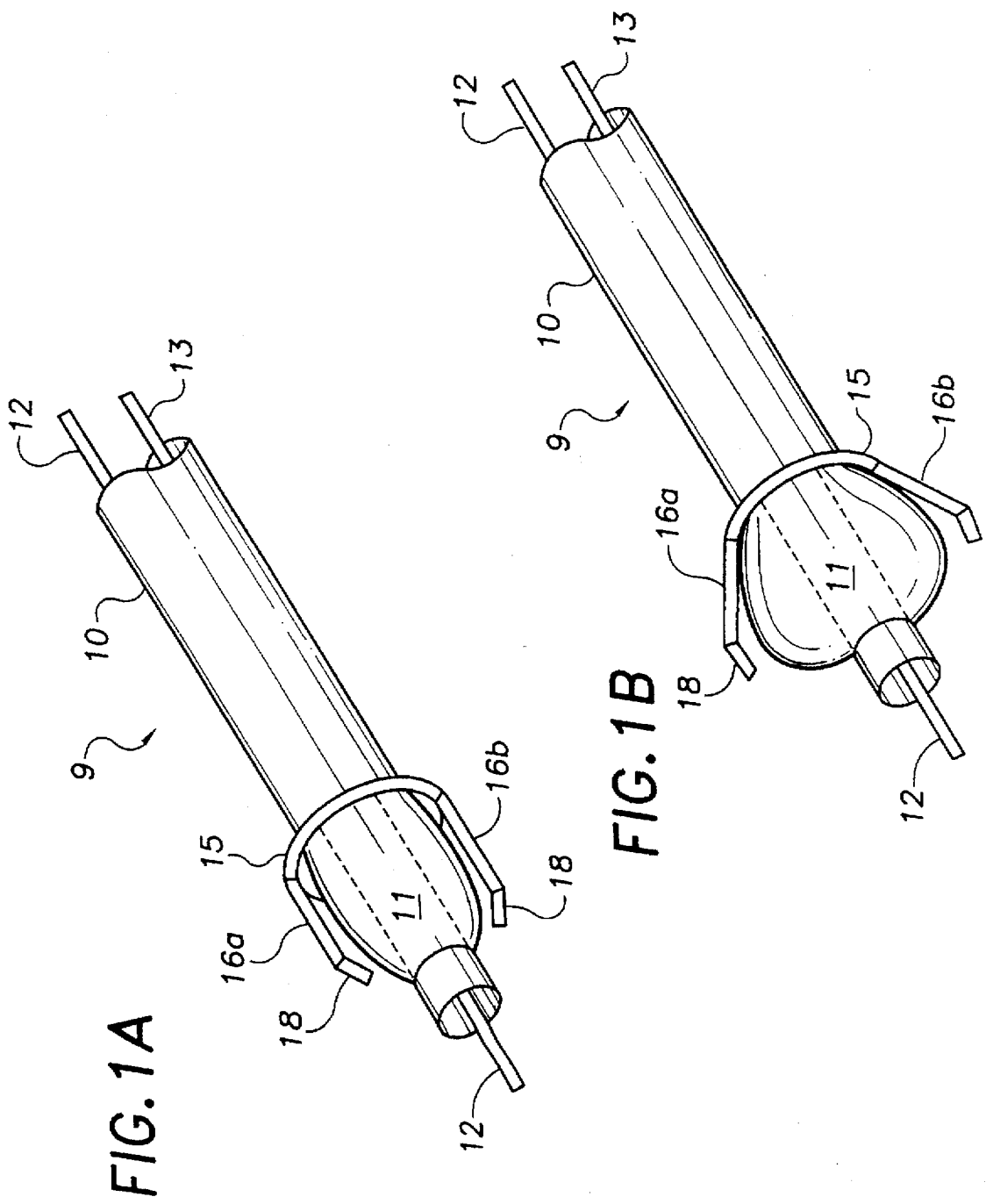

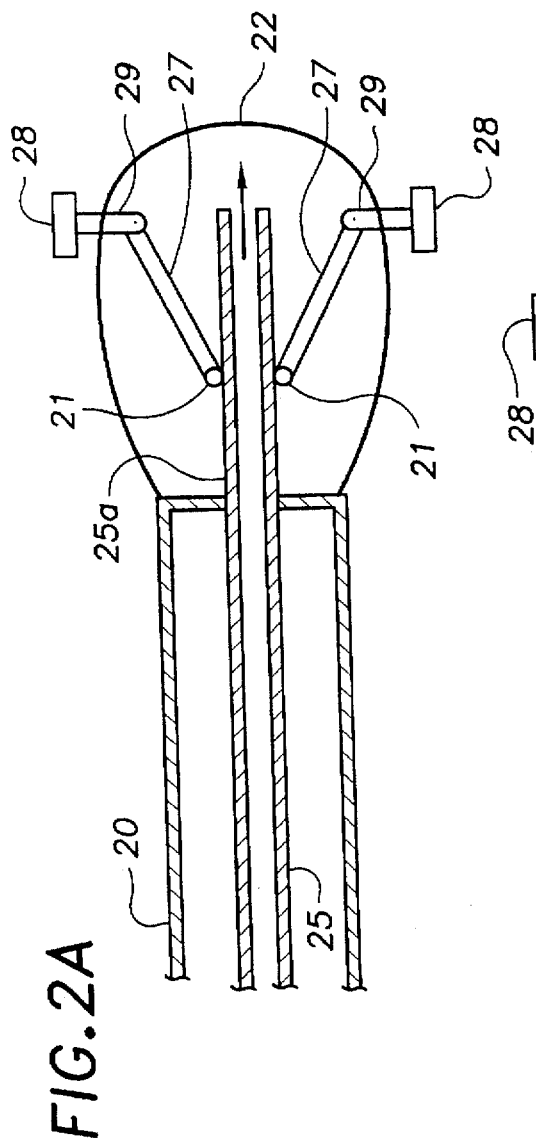
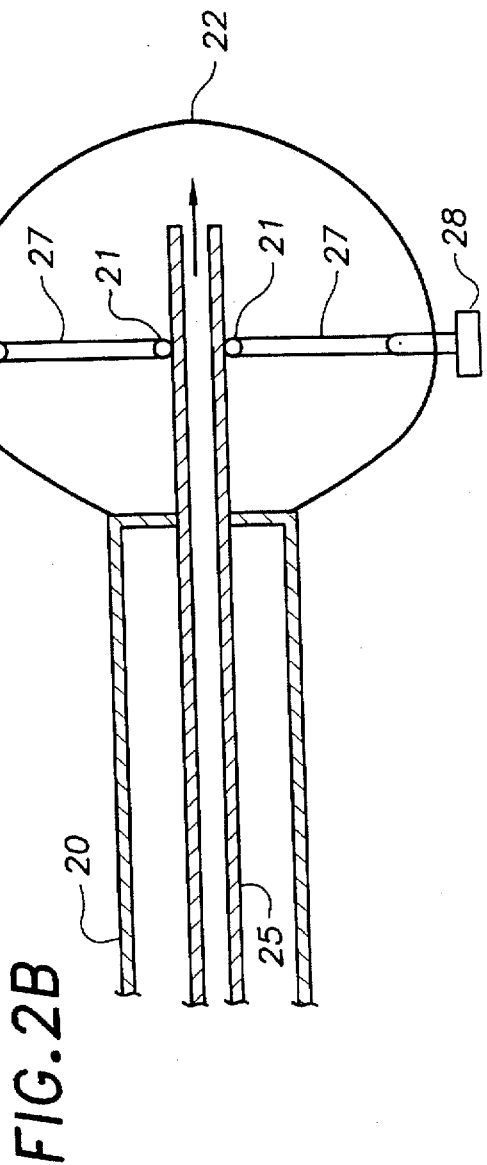
FIG.2A
FIG.2B

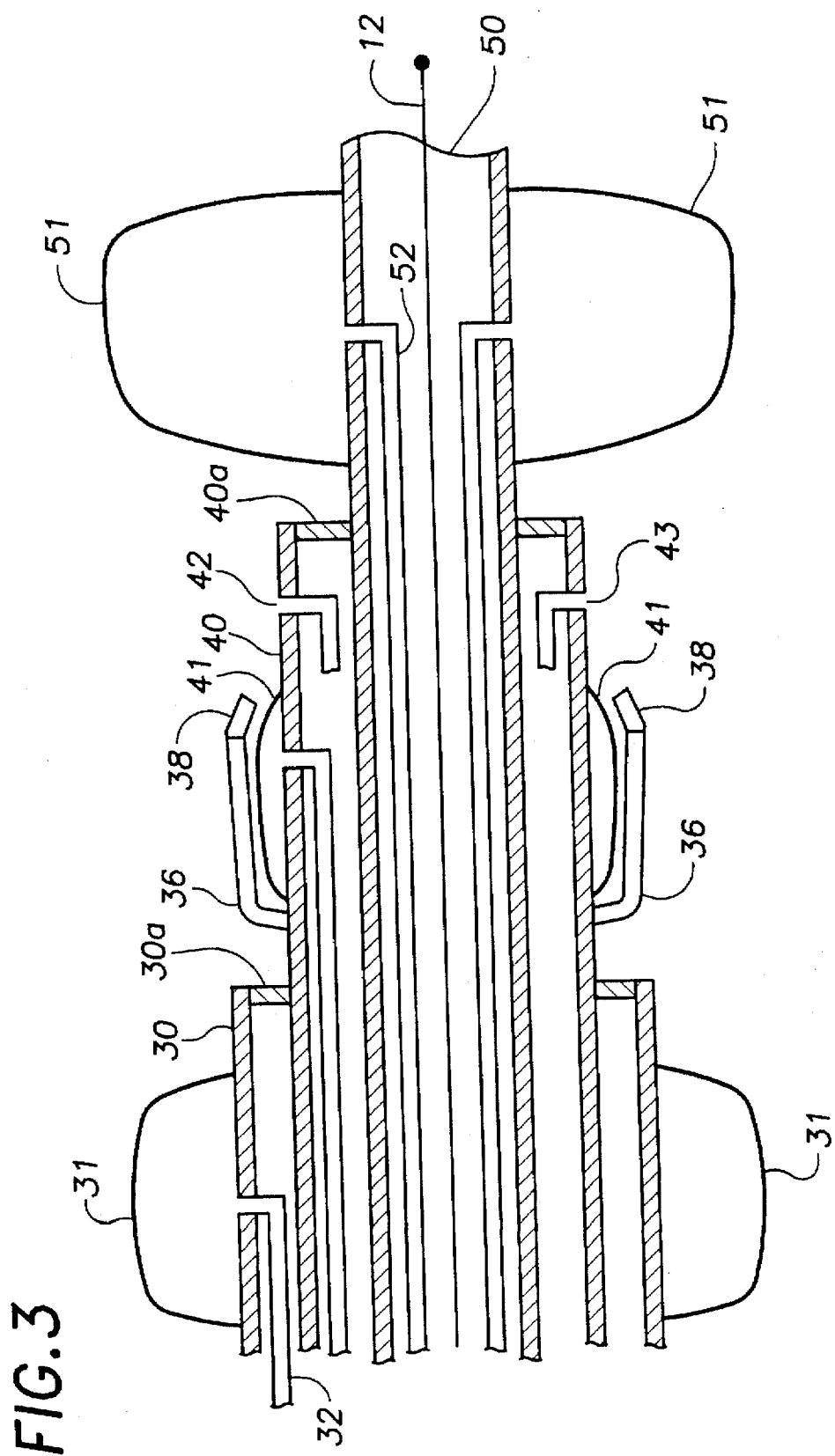

BALLOON ACTUATED CATHETER

BACKGROUND AND SUMMARY OF THE INVENTION

Arteriosclerosis is a general term which refers to any of a group of diseases in which the lumen of an artery becomes narrowed or blocked. The most common and important form of arteriosclerosis, especially in Western societies, is the disease known as atherosclerosis. In atherosclerosis, there is an accumulation of lipids in the intimal (ie., inner) layer of the affected artery. The resulting intimal thickening restricts the flow of blood so as to hinder the functioning of or permanently damage the organ which the artery feeds. These accumulations of lipids tend to be localized and can occur in coronary, cerebral or peripheral arteries. They will hereinafter be referred to synonymously as lesions, plaques, or atheromas.

Such lipid accumulation is made up of free lipid and smooth muscle cells which have proliferated and taken up lipid. As the disease progresses, the lesion may begin to absorb calcium that causes it to harden. The plaque may also be composed of blood which has clotted in response to the presence of the atheroma. Although the process of plaque formation is not completely understood, it is known to be progressive, and the atherosclerotic plaques may vary greatly in their physical characteristics. Another cause of arterial narrowing, especially in patients having an acute myocardial infarction (ie., a heart attack), is the formation of a thrombus or blood clot within a coronary artery.

Treatment of atherosclerosis and occlusive thrombi is aimed at alleviating the diminished blood flow. This can sometimes be done by medical means which cause the smooth muscles of the arterial walls to relax and there by dilate the artery. Other treatment methods are directed toward physiological compensation for the reduced blood flow. In cases where the artery is severely occluded, however, there is no reasonable alternative but to try to reestablish a lumen of proper diameter. A number of surgical procedures have been developed toward this end. They include endarterectomy, in which plaque or thrombus is surgically removed, and by-pass grafts, in which a segment of artery or vein from elsewhere in the body is removed and reattached in place of the occluded artery. These procedures are major surgical operations and present a number of disadvantages to a patient, including high financial cost, inconvenience, and the risk of complications associated with any major surgery. Therefore, in the past several years, methods of reestablishing the patency of an occluded artery have been developed which are relatively noninvasive and present less risk to a patient than conventional surgery. One such method is transluminal angioplasty. Other parts of the body are subject to balloon dilation, such as the esophagus and urethra, which may have narrowing due to scarring or fibromuscular hyperplasia, which is abnormal inward growth of the normal living tissue of an artery or other vessel.

The conventional method of performing transluminal angioplasty uses a special double lumen catheter. The first or inner lumen allows passage of a guide wire. Concentric or adjacent with this lumen is a second lumen which connects to a sausage-shaped segment of tubing or balloon at the distal end of the catheter. The second lumen and balloon are generally filled with diluted contrast media. Contrast media is radio-opaque liquid which makes visualization of the catheter possible by means of X-rays. The procedure first involves selecting a convenient place to introduce the catheter into the arterial system of the patient, such as the fern oral artery of the leg. Next, the catheter is guided to the blocked artery. This is done manually and with the aid of an X-ray monitor. When the catheter is appropriately positioned, the guide wire is advanced to and past the point of obstruction. The balloon catheter, which surrounds the guide wire, is then advanced along with the guide wire until it is surrounded by the occluding plaque. The balloon, made of material with high tensile strength and low elasticity, is inflated to a pressure as high as 15 atmospheres. As the balloon expands, it creates a larger inner diameter within the occluded artery. It is not known with certainty what physical processes occur within the occluded artery in response to the balloon inflation, but the usual method is to inflate the balloon to a certain predetermined pressure and repeat the inflation an arbitrary number of times. The balloon is then collapsed and retracted. The site of the obstruction is then examined angiographically and, if the artery is still occluded, a decision is made either to repeat the angioplasty procedure or to resort to some other option.

One of the primary problems associated with transluminal angioplasty procedures, however, is that of restenosis. A large proportion of arteries rendered patent by means of angioplasty become occluded again some time later. The mechanism of such restenosis is not completely understood and may be different for different types of atheromas. In order to at least partially overcome the restenosis problem, atherectomy procedures have been developed in which plaque is mechanically cut from the arterial wall by means of a cutting device at the end of a catheter. Atherectomy may be performed as either an alternative or adjunct to conventional angioplasty in which brittle, undeformable plaque is removed from the lesion before proceeding with balloon dilation of the artery.

One of problems associated with atherectomy catheters is the restriction on the cutting radius of the device brought about by size of the entry site. Furthermore, if the cutting blades of the catheter extend to the desired cutting radius while the catheter is being maneuvered into position, the cutting blades may encumber the passage of the catheter through the blood vessels as well as present a risk of causing an inadvertent injury. For these reasons, atherectomy catheters have been developed with retractable cutting blades. Examples of such catheters include U.S. Pat. Nos. 5,224,945 and 5,224,949 the disclosures of which are hereby incorporated by reference. Both of those devices, however, depend upon applying a pulling force to a wire or similar structure within the catheter in order to mechanically operate a retraction/extension mechanism. Applying such a pulling force to a catheter, however, is difficult when the catheter is contorted within the patient's arterial system. Either a sufficient force for operating the retraction/extension mechanism will not be able to be applied or traumatic injury may be produced to the blood vessels.

The present invention is a catheter device for performing atherectomy procedures and similar operations within a blood vessel or other body duct in which a retraction/extension mechanism is actuated by the application of fluid pressure to an expandable balloon. The balloon is secured to the distal end of a flexible tube having a fluid passageway within the tube for conducting a fluid to expand the balloon, and a cutting device or blade is mounted on the distal end of the tube and disposed so that such device or cutting blade is radially extended as the balloon is expanded. In one embodiment, cutting blades are mounted on the ends of resilient blade support arms that extend axially along the wall of the catheter tube. In another embodiment, the blade support arms are pivotably mounted on a support structure within the balloon with the cutting blades mounted on structures that protrude through the wall of the balloon to the exterior. In another embodiment, two additional inflatable balloons are mounted on the catheter on both sides of the cutting blades for isolating the region therebetween or supporting portions of the body duct on both sides of the portion to be operated on.

It is therefore a primary object of the present invention to provide a catheter having extendable cutting blades for performing atherectomy procedures within blood vessels and similar procedures within other body ducts.

It is a further object to provide for the cutting blades of a catheter to be extendable by the application of fluid pressure to the catheter that inflates a balloon operable to extend the cutting blades when so inflated.

Other objects, features, and advantages of the invention will become evident in light of the following detailed description considered in conjunction with the referenced drawings of preferred exemplary embodiments according to the present invention.

BRIEF DESCRIPTION OF THE DRAWINGS

FIGS. 1A and 1B are depictions of one embodiment of a balloon actuated catheter with the cutting blades in the closed and extended positions, respectively.

FIGS. 2A and 2B are cross-sectional views of another embodiment of a balloon actuated catheter with the cutting blades in the closed and extended positions, respectively.

FIG. 3 shows in cross-section a balloon actuated catheter having two balloons for isolating an operative site therebetween.

DETAILED DESCRIPTION OF THE INVENTION

Illustrated in FIGS. 1A and 1B is an embodiment of the present invention in which a catheter device 9 includes an elongated flexible tubular structure 10 having an expandable balloon 11 secured around its distal end. The distal end of the catheter is inserted into a blood vessel or other body duct in which it is desired to perform an atherectomy or other cutting procedure while the proximal end extends backward out of the vessel. A guide wire 12 is shown running through the lumen of the tubular structure 10 and typically is guided to the operative site by radiographic means with the tubular structure then slid over the wire in so-called "over the wire" fashion until the distal end of the catheter is positioned at the operative site. Either secured to or integral with the tubular structure 10 is an annular collar 15 to which are mounted one or more cutting blades 18 by means of blade support arms 16. Each of the blade support arms 16a and 16b is a resilient structure such as a cantilevered flat leaf spring that extends along the side of the tubular structure 10 in an axial direction. The resilience of the arms 16a and 16b maintains each arm in an axial orientation so that it lies close to the surface of the tubular structure 10 so that the blade 18 is normally in a retracted position as shown in FIG. 1A. Balloon 11 when uninflated underlies the support arms 16 and may be, for example, a cuff-type balloon wrapped around the distal end of the tubular structure 10 or may be a balloon extending axially from the distal end. In fluid communication with the interior of balloon 11 is a conduit 13 that extends from the balloon 11 out through the proximal end of the catheter to provide a passageway for inflating and deflating the balloon with a fluid such as saline solution.

FIG. 1B shows the catheter with the blades 18 in an extended and operable position whereby expansion of balloon 11 has forced the blade support arms 16 radially outward to thereby operatively extend the cutting blades 18. Balloon 11 is constructed of a material that will withstand sufficient wall tension to generate a pressure inside the balloon great enough to force the blade support arms 16 laterally. With the balloon 11 deflated, the catheter is able to be positioned at the operative site without being encumbered by the extended cutting blades. Once the distal end is correctly positioned, the cutting blades may be extended simply by inflation of balloon 11. In order to cut plaque from the artery walls, the blades 18 are rotated by applying a torque to the proximal end of the tubular structure 10. Alternatively, vibrational energy may be transmitted to the blades 18 either directly by vibrating the tubular structure 10 or by operation of an electrical transducer (eg., an electromagnetic or piezoelectric vibrator) that vibrates the blades 18 or blade support arms 16. The cutting action may also be provided by edges or sharpened portions of the support arms 16.

FIGS. 2A and 2B show an alternate embodiment of a balloon actuated atherectomy catheter comprising an assembly of a flexible tube 20 to which an expandable balloon 22 is secured at the distal end thereof. A flexible conduit 25 in fluid communication with the interior of the balloon 22 extends through the lumen of tube 20 toward its proximal end where fluid pressure may be applied to inflate the balloon. A rigid support structure 25a extends from tube 20 into the balloon 22, upon which are mounted one or more blade support arms 27. In this particular embodiment, support structure 25a is an extension of the conduit 25 but may also be a separate structure. Pivotally attached to the distal end of blade support arm 27 is a tab extension 29 that sealingly protrudes though a wall portion of the balloon 22 to reach the exterior. Secured to the portion of each of the tab extensions 29 located external to the balloon are cutting blades 28 that may either be in a retracted position near the radius of the tube 20 or extended radially outward in a cutting position. The proximal ends of the blade support arms 27 are pivotally attached to the support structure 25a and biased in an axial direction by means of springs 21 so as to force the blades 28 radially inward and to maintain them in a retracted position as shown in FIG. 2A. FIG. 2B shows balloon 22 in an inflated state that has forced the blade support arms 27 to pivot outwardly and extend the cutting blades 28. Because blade support arms 27 are pivotable only in an axial direction and not tangentially, they provide a rigid support for the blades 28 when resistance is encountered from cutting plaque as the tube 20 is rotated.

FIG. 3 shows an embodiment of a balloon actuated atherectomy catheter of the dual-balloon type. The catheter comprises a flexible tube 40 to the distal end of which is wrapped around a cuff-type balloon 41. Exterior to the balloon 41 and extending in an axial direction adjacent the balloon are one or more blade support arms 36 mounted to the tube 40. Blade support arms 36 are cantilevered resilient structures that are attached to the tube 40 and biased so as to resist being forced outwardly. At the distal end of each blade support arm 36 is formed or secured a cutting blade 38. A conduit 42 extends though the lumen of tube 40 and is in fluid communication with the interior of balloon 41. Application of fluid pressure to the proximal end of conduit 42 inflates the balloon 41 and extends the cutting blades outwardly as described above with reference to FIGS. 1A and 1B. Additional cuff-type balloons 51 and 31 are provided for isolating the operative site during the cutting procedure so that cutting debris may be contained in the isolated artery portion and not left to be carried further downstream and where it may possibly occlude a small vessel. Balloon 31 is a cuff-type balloon wrapped around a tube 30 while balloon 51 is a similar cuff-type balloon wrapped around a tube 50. Conduits 32 and 52 within the lumena of tubes 30 and 50 are provided for inflating balloons 31 and 51, respectively. The catheter is thus seen to comprise three tubular structures concentrically arranged. The innermost tube 50 (through the lumen of which runs a guide wire 12) resides within tube 40 and extends out through the proximal end of tube 40. The distal end of tube 40 is sealed to tube 50 by means of a sealing ting 40a that allows tube 40 to be rotated with respect tube 50. The distal end of outermost tube 30 is similarly rotatably mounted around tube 40 by means of sealing ring 30a. The operation of the catheter is as follows. After the catheter is maneuvered to the operative site with the cutting blades disposed adjacent the lesion to be operated on, balloons 31 and 51 are inflated to isolate that portion of the artery from the rest of the circulation. The inflation of balloons 31 and 51 against the arterial walls also serves to fix the positions of tubes 30 and 50. After extension of cutting blades 38 by expanding balloon 41, tube 40 is rotated by applying a torque to the proximal end of tube 40 to produce a cutting action that slices plaque from the arterial wall. Because of the rotatable mounting of the tubes within one another, tube 40 is able to be freely rotated even though tubes 30 and 50 are fixed in place by balloons 31 and 51, respectively. After a cutting operation, a flushing solution and suction may be applied to the region isolated between the balloons by means of conduits 42 and 43 in order to remove cutting debris. The balloons may then be deflated and the catheter removed.

Blades 18, 28, and 38 may be supplemented or replaced with fine abrasive bits cemented to the respective support arms or to the outside surfaces of the balloons 11, 22, and 41. The blades may also be directly cemented or molded integral with the walls of the balloons. Also, one or more miniature electric motors mounted in the operating head of the catheter may be employed to rotate and/or extend and retract the cutting blades.

Although the invention has been described in conjunction with the foregoing specific embodiment, many alternatives, variations, and modifications will be apparent to those of ordinary skill in the art. Those alternatives, variations, and modifications are intended to fall within the scope of the following appended claims.

What is claimed is:

1. A catheter device for performing atherectomy procedures and the like within a blood vessel or other body duct comprising:
   (a) a first elongated tubular structure having an operating end for insertion into a body duct;
   (b) a first expandable balloon secured to the operating end of said first tubular structure;
   (c) a cutting tool mounted at the operating end of said tubular structure and disposed so that said cutting tool is radially extended as said first balloon is expanded;
   (d) second and third expandable balloons rotatably connected to said first elongate tubular structure located adjacent to and on each side of said cutting tool whereby expansion of said second and third balloons isolates the region therebetween containing said cutting tool; and
   (e) wherein said cutting tool is rotatable with respect to said second and third balloons to cut tissue.

2. A catheter device in accordance with claim 1 wherein said cutting tool is a cutting blade.

3. A catheter device in accordance with claim 1 wherein said cutting tool comprises abrasive bits.

4. A catheter device in accordance with claim 1 wherein said first balloon is in fluid communication with the interior of said first tubular structure so as to allow inflation of said first balloon by the application of fluid pressure to the interior said tubular structure.

5. A catheter device in accordance with claim 1 further comprising a plurality of cutting blades mounted on the operating end of said first tubular structure and disposed so that said cutting blades are outwardly extended as said first balloon is expanded.

6. A catheter device in accordance with claim 1 further comprising a fluid passageway within said first tubular structure communicating with the proximal and distal ends of said structure for infusion of a flushing liquid to an operative site.

7. A catheter device in accordance with claim 1 further comprising a second tubular structure within which said first tubular structure is coaxially mounted, said second tubular structure having said second expandable balloon mounted in the proximity of its operating end, and having a second fluid passageway therein in fluid communication with the interior of said second balloon for passing a fluid therethrough to expand said second balloon, and wherein expansion of said second balloon against the walls of a body duct serves to fix the position of said second tubular structure within the duct.

8. A catheter device in accordance with claim 7 wherein said first tubular structure is rotatable within said second tubular structure so as to cause rotation of said cutting blade.

9. A catheter device in accordance with claim 8 further comprising a third tubular structure coaxially and rotatably mounted within said first tubular structure, said third tubular structure having said third expandable balloon mounted in the proximity of its distal end, and having a third fluid passageway therein in fluid communication with the interior of said third balloon for passing a fluid therethrough to expand said third balloon, and wherein expansion of said second and third balloons against the walls of a body duct serves to isolate an operative site therebetween for performance of a cutting procedure by said cutting blade.

10. A catheter device in accordance with claim 9 further comprising fourth fluid passageway in said first tubular structure in fluid communication with a port on said first tubular structure disposed between said second and third balloons for infusion of a flushing liquid to the operative site.

11. A catheter device in accordance with claim 10 further comprising a fifth fluid passageway in said first tubular structure in fluid communication with a port on said first tubular structure disposed between said second and third balloons for suctioning of cut debris from the operative site.

12. A catheter device in accordance with claim 9 further comprising a cantilevered strip attached to said first tubular structure at one end and having a cutting blade at its other end, wherein said strip extends axially from its point of attachment to said first tubular structure so as to be disposed next to said first balloon so that expansion of said balloon causes said strip and said cutting blade to be extended radially from said first tubular structure.

13. A catheter device in accordance with claim 9 further comprising a plurality of cutting blades mounted at the end of said first tubular structure and radially extendable as the first balloon is expanded.

* * * * *